(12) United States Patent
Vann et al.

(10) Patent No.: US 9,235,682 B2
(45) Date of Patent: Jan. 12, 2016

(54) COMBINED EPISODIC AND CONTINUOUS PARAMETER MONITORING

(75) Inventors: John Raymond Vann, Auburn, NY (US); Robert Paul Wilmington, Vancouver, WA (US); Thomas A. Myers, Syracuse, NY (US); Gregory P. Vassallo, Camillus, NY (US); Edward Imboden, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 69 days.

(21) Appl. No.: 13/440,318

(22) Filed: Apr. 5, 2012

(65) Prior Publication Data

US 2013/0265327 A1  Oct. 10, 2013

(51) Int. Cl.
G09G 5/00 (2006.01)
G06F 19/00 (2011.01)
A61B 5/00 (2006.01)

(52) U.S. Cl.
CPC ........... G06F 19/3406 (2013.01); A61B 5/7445 (2013.01); A61B 2505/03 (2013.01); G06F 19/3487 (2013.01); G09G 2380/08 (2013.01)

(58) Field of Classification Search
None
See application file for complete search history.

(56) References Cited

U.S. PATENT DOCUMENTS

| 5,140,519 | A | 8/1992 | Friesdorf et al. |
| D366,460 | S | 1/1996 | Jorenson |
| 5,701,894 | A | 12/1997 | Cherry |
| D427,574 | S | 7/2000 | Sawada |
| 6,219,046 | B1 | 4/2001 | Thomas et al. |
| D454,139 | S | 3/2002 | Feldcamp |
| 6,364,834 | B1 | 4/2002 | Reuss |
| 6,398,727 | B1 | 6/2002 | Bui |
| 6,416,471 | B1 | 7/2002 | Kumar |
| 6,469,717 | B1 | 10/2002 | Wineke |
| D465,226 | S | 11/2002 | Friedman |
| D468,322 | S | 1/2003 | Walker et al. |

(Continued)

FOREIGN PATENT DOCUMENTS

| CN | 1356783 A | 7/2002 |
| CN | 1649538 A | 8/2005 |

(Continued)

OTHER PUBLICATIONS

Al-Qutayri et al.; Framework for Secure Wireless Health monitoring and remote Access System, Inderscience Enterprises Ltd. copyright 2010, 19 pages.

(Continued)

*Primary Examiner* — Tize Ma
*Assistant Examiner* — Yu Chen
(74) *Attorney, Agent, or Firm* — Merchant & Gould P.C.

(57) ABSTRACT

A method for displaying physiological data on a medical display device includes receiving one or more first units of physiological data from a first monitoring device. At least one of the first units of physiological data is received on a continuous basis. Each first unit of physiological data corresponds to a medical parameter being monitored by the first monitoring device. One or more second units of physiological data are received from a second monitoring device. At least one of the second units of physiological data is received on a non-continuous basis. Each second unit of physiological data corresponds to a medical parameter being monitored by the second monitoring device. The first and second units of physiological data are displayed on a single display screen of the medical display device.

15 Claims, 14 Drawing Sheets

(56) References Cited

U.S. PATENT DOCUMENTS

| | | |
|---|---|---|
| 6,535,714 B2 | 3/2003 | Melker |
| 6,658,276 B2 | 12/2003 | Kiani et al. |
| 6,675,031 B1 | 1/2004 | Porges |
| 6,707,476 B1 | 3/2004 | Hochstedler |
| 6,783,573 B2 | 8/2004 | Richardson |
| 6,828,910 B2 | 12/2004 | VanRyzin |
| D510,582 S | 10/2005 | Hoang |
| D523,440 S | 6/2006 | Hernandez |
| D525,982 S | 8/2006 | Suzuki |
| D527,011 S | 8/2006 | Bixler |
| 7,124,366 B2 | 10/2006 | Foreman et al. |
| 7,134,994 B2 | 11/2006 | Alpert |
| D545,829 S | 7/2007 | Fletcher |
| 7,336,187 B2 | 2/2008 | Hubbard |
| D575,296 S | 8/2008 | Fairfield |
| 7,409,399 B2 | 8/2008 | Miyamoto |
| D576,634 S | 9/2008 | Clark |
| D579,456 S | 10/2008 | Chen et al. |
| 7,433,827 B2 | 10/2008 | Rosenfeld et al. |
| D586,818 S | 2/2009 | Luck |
| D590,413 S | 4/2009 | Bhat et al. |
| D590,414 S | 4/2009 | Bhat et al. |
| D592,156 S | 5/2009 | Drews et al. |
| D592,675 S | 5/2009 | Bhat |
| 7,565,616 B2 | 7/2009 | Buchmann |
| D598,923 S | 8/2009 | Chen et al. |
| D598,929 S | 8/2009 | Bhat |
| D599,358 S | 9/2009 | Hoefnagels et al. |
| D599,398 S | 9/2009 | Laidlaw |
| D603,416 S | 11/2009 | Poling |
| D607,463 S | 1/2010 | Krieter |
| D608,366 S | 1/2010 | Matas |
| 7,662,106 B2 | 2/2010 | Daniels |
| D612,860 S | 3/2010 | Tarara |
| RE41,236 E | 4/2010 | Seely |
| D614,634 S | 4/2010 | Nilson |
| 7,765,479 B2 | 7/2010 | Goodwin et al. |
| 7,774,060 B2 | 8/2010 | Westenskow |
| 7,782,302 B2 | 8/2010 | Lee et al. |
| 7,787,946 B2 | 8/2010 | Stahmann et al. |
| 7,810,497 B2 | 10/2010 | Pittman |
| D632,699 S | 2/2011 | Judy |
| 7,895,527 B2 | 2/2011 | Zaleski |
| D635,150 S | 3/2011 | Sykes |
| D637,603 S | 5/2011 | Godgart |
| 7,937,134 B2 | 5/2011 | Uber |
| D640,264 S | 6/2011 | Fujii |
| 7,967,759 B2 | 6/2011 | Couvillon |
| D643,043 S | 8/2011 | Loken |
| 8,001,967 B2 | 8/2011 | Wallace |
| 8,020,558 B2 | 9/2011 | Christopher |
| D646,689 S | 10/2011 | Ulliot |
| 8,028,701 B2 | 10/2011 | Al-Ali |
| 8,038,593 B2 | 10/2011 | Friedman |
| 8,046,705 B2 | 10/2011 | Hunleth et al. |
| 8,055,514 B2 | 11/2011 | Elsholz |
| 8,078,983 B2 | 12/2011 | Davis |
| D652,051 S | 1/2012 | Judy |
| D656,153 S | 3/2012 | Imamura |
| D656,157 S | 3/2012 | Khan |
| D656,946 S | 4/2012 | Judy |
| D657,368 S | 4/2012 | Magee |
| D658,196 S | 4/2012 | Wood et al. |
| D658,667 S | 5/2012 | Cho |
| D664,971 S | 8/2012 | Lee et al. |
| D664,984 S | 8/2012 | Lee et al. |
| D666,625 S | 9/2012 | Gilmore et al. |
| D667,837 S | 9/2012 | Magee |
| D667,838 S | 9/2012 | Magee et al. |
| D674,401 S | 1/2013 | Trumble et al. |
| D675,218 S | 1/2013 | Arnold et al. |
| D676,863 S | 2/2013 | Ho Kushner et al. |
| D676,864 S | 2/2013 | Velasco et al. |
| D688,685 S | 8/2013 | Rhee et al. |
| D689,899 S | 9/2013 | Lee et al. |
| D695,781 S | 12/2013 | Edwards et al. |
| 8,732,604 B2 | 5/2014 | Okamoto et al. |
| 2002/0054141 A1 | 5/2002 | Yen et al. |
| 2002/0078097 A1 | 6/2002 | Chen et al. |
| 2002/0126137 A1 | 9/2002 | Kaestner, Jr. |
| 2002/0177758 A1 | 11/2002 | Schoenberg et al. |
| 2003/0060727 A1 | 3/2003 | Kline |
| 2003/0135087 A1 | 7/2003 | Hickle et al. |
| 2004/0002874 A1 | 1/2004 | Shaffer et al. |
| 2004/0088199 A1 | 5/2004 | Childress et al. |
| 2004/0111045 A1 | 6/2004 | Sullivan et al. |
| 2005/0114374 A1 | 5/2005 | Juszkiewicz et al. |
| 2005/0229110 A1 | 10/2005 | Gegner et al. |
| 2005/0288571 A1 | 12/2005 | Perkins |
| 2006/0149597 A1 | 7/2006 | Powell et al. |
| 2006/0200009 A1* | 9/2006 | Wekell et al. ............ 600/300 |
| 2006/0228096 A1 | 10/2006 | Hoshino et al. |
| 2006/0229557 A1 | 10/2006 | Fathallah et al. |
| 2006/0247948 A1 | 11/2006 | Ellis et al. |
| 2007/0000494 A1 | 1/2007 | Banner et al. |
| 2007/0067005 A1 | 3/2007 | Schatz et al. |
| 2007/0150810 A1 | 6/2007 | Katz et al. |
| 2007/0156456 A1 | 7/2007 | McGillin et al. |
| 2007/0167173 A1 | 7/2007 | Halcrow et al. |
| 2007/0167694 A1 | 7/2007 | Causevic et al. |
| 2007/0174079 A1 | 7/2007 | Kraus |
| 2007/0185390 A1 | 8/2007 | Perkins et al. |
| 2007/0197878 A1 | 8/2007 | Shklarski |
| 2007/0203744 A1 | 8/2007 | Scholl |
| 2007/0215157 A1 | 9/2007 | Straw |
| 2007/0276261 A1 | 11/2007 | Banet et al. |
| 2008/0012833 A1 | 1/2008 | Beck et al. |
| 2008/0021379 A1 | 1/2008 | Hickle |
| 2008/0055074 A1 | 3/2008 | Gao et al. |
| 2008/0058609 A1 | 3/2008 | Garibaldi et al. |
| 2008/0058614 A1 | 3/2008 | Banet et al. |
| 2008/0072896 A1 | 3/2008 | Setzer et al. |
| 2008/0077026 A1 | 3/2008 | Banet et al. |
| 2008/0086691 A1 | 4/2008 | Hopermann et al. |
| 2008/0103375 A1* | 5/2008 | Kiani ..................... 600/323 |
| 2008/0115081 A1 | 5/2008 | Sankaravadivelu et al. |
| 2008/0155406 A1 | 6/2008 | Naka |
| 2008/0208812 A1 | 8/2008 | Quoc et al. |
| 2008/0229248 A1 | 9/2008 | Fagans et al. |
| 2008/0249377 A1 | 10/2008 | Molducci et al. |
| 2008/0249801 A1 | 10/2008 | Zaleski |
| 2008/0281168 A1* | 11/2008 | Gibson et al. ............ 600/301 |
| 2008/0281637 A1 | 11/2008 | Matz |
| 2008/0318529 A1 | 12/2008 | Harb |
| 2009/0005651 A1 | 1/2009 | Ward et al. |
| 2009/0054743 A1 | 2/2009 | Stewart |
| 2009/0054798 A1 | 2/2009 | Varney et al. |
| 2009/0112630 A1 | 4/2009 | Collins, Jr. et al. |
| 2009/0131761 A1 | 5/2009 | Moroney, III et al. |
| 2009/0132588 A1 | 5/2009 | Mahesh et al. |
| 2009/0143652 A1 | 6/2009 | Warburton et al. |
| 2009/0149927 A1 | 6/2009 | Kneuer et al. |
| 2009/0158415 A1 | 6/2009 | Dillon |
| 2009/0240116 A1 | 9/2009 | Bluth |
| 2009/0240193 A1 | 9/2009 | Mensinger et al. |
| 2009/0241958 A1 | 10/2009 | Baker, Jr. |
| 2009/0275805 A1 | 11/2009 | Lane et al. |
| 2009/0275810 A1 | 11/2009 | Ayers et al. |
| 2009/0282340 A1 | 11/2009 | Akaike et al. |
| 2009/0306482 A1 | 12/2009 | Davis et al. |
| 2009/0306488 A1 | 12/2009 | Al-Ali et al. |
| 2009/0312648 A1 | 12/2009 | Zhang et al. |
| 2010/0050075 A1 | 2/2010 | Thorson et al. |
| 2010/0069004 A1 | 3/2010 | Bioebaum |
| 2010/0094096 A1 | 4/2010 | Petruzzelli et al. |
| 2010/0097380 A1 | 4/2010 | Daniels et al. |
| 2010/0218766 A1 | 9/2010 | Milne |
| 2010/0274098 A1 | 10/2010 | Belford et al. |
| 2010/0324380 A1* | 12/2010 | Perkins et al. ............ 600/301 |
| 2011/0010621 A1 | 1/2011 | Wallaert et al. |
| 2011/0015502 A1 | 1/2011 | Peyser |
| 2011/0071420 A1 | 3/2011 | St. Pierre |
| 2011/0169644 A1 | 7/2011 | Muhsin et al. |
| 2011/0190600 A1 | 8/2011 | McKenna et al. |

(56) References Cited

U.S. PATENT DOCUMENTS

| | | | |
|---|---|---|---|
| 2011/0205577 A1 | 8/2011 | Mori et al. | |
| 2011/0209707 A1 | 9/2011 | Terhark | |
| 2011/0227739 A1 | 9/2011 | Gilham et al. | |
| 2011/0245630 A1 | 10/2011 | St. Pierre | |
| 2011/0246565 A1 | 10/2011 | Irwin et al. | |
| 2011/0276338 A1 | 11/2011 | Warner et al. | |
| 2011/0290250 A1 | 12/2011 | Olson et al. | |
| 2011/0313301 A1 | 12/2011 | Lane et al. | |
| 2012/0000470 A1 | 1/2012 | Milne et al. | |
| 2012/0016251 A1 | 1/2012 | Zhang et al. | |
| 2012/0048090 A1 | 3/2012 | Etter et al. | |
| 2012/0095778 A1* | 4/2012 | Gross et al. | 705/2 |
| 2012/0096367 A1 | 4/2012 | DelloStritto et al. | |
| 2012/0110444 A1 | 5/2012 | Li et al. | |
| 2012/0117099 A1 | 5/2012 | Gross | |
| 2012/0215075 A1 | 8/2012 | Surace et al. | |
| 2012/0296183 A1 | 11/2012 | Kinsley et al. | |
| 2013/0151285 A1 | 6/2013 | McLaren et al. | |
| 2013/0267792 A1 | 10/2013 | Petersen et al. | |
| 2013/0267793 A1 | 10/2013 | Meador | |
| 2013/0267861 A1 | 10/2013 | Vassallo et al. | |
| 2013/0268283 A1 | 10/2013 | Vann et al. | |
| 2013/0293373 A1* | 11/2013 | Gegner et al. | 340/527 |
| 2013/0311926 A1 | 11/2013 | Keegan et al. | |
| 2014/0040429 A1 | 2/2014 | Irwin et al. | |
| 2014/0098209 A1 | 4/2014 | Neff | |
| 2014/0108041 A1 | 4/2014 | Bechtel et al. | |
| 2014/0135588 A1 | 5/2014 | Al-Ali et al. | |

FOREIGN PATENT DOCUMENTS

| | | |
|---|---|---|
| CN | 101069638 A | 11/2007 |
| EP | 0707824 A2 | 4/1996 |
| EP | 2 093 683 A2 | 8/2009 |
| GB | 2409951 A | 7/2005 |
| JP | 10-091687 A | 4/1998 |
| JP | 03682617 B2 | 8/2005 |
| JP | 2010-015193 A | 1/2010 |
| WO | 2010-026021 | 4/2001 |
| WO | 0126021 A1 | 4/2001 |
| WO | 2001-089362 | 5/2001 |
| WO | 2006076498 A2 | 7/2006 |
| WO | 2010/102069 A2 | 9/2010 |
| WO | 201100132 A1 | 1/2011 |
| WO | 2011001302 A1 | 1/2011 |

OTHER PUBLICATIONS

Kozlovszky et al.; Network and Service Management and Diagnostics Solution of a Remote Patient Monitoring System, IEEE copyright 2011, 4 pages.

Lamberti et al.; Ubiquitous Real-Time Monitoring of Critical-Care Patients in Intensive Care Units, IEEE copyright 2003, 4 pages.

Panorama™ Central Station, Surgical Product Guide copyright 2011, 2 pages.

Zhao et al.; A Portable, Low-Cost, Battery-Powered Wireless Monitoring System for Obtaining Varying Physiologic Parameters from Multiple Subjects, IEEE copyright 2006, 4 pages.

International Search Report and Written Opinion in PCT/US2013/031486 mailed Jun. 28, 2013, 10 pages.

International Search Report and Written Opinion in PCT/US2013/031458 mailed Jun. 28, 2013, 10 pages.

Adams, A.P., Breathing System Disconnections, Br. J. Anaesth, 1994, vol. 73, No. 1, pp. 46-54.

Capnography: An Objective Tool for Assessing Respiratory Status, Physio-Control, Inc., 2008, pp. 1-8.

Colin Prodigy Press-Mate Prodigy II® Portable Vital Signs Monitors, DRE, Copyright 2009, accessed at: http://www.dremed.com/catalog/product_info.php/products_id/1181; 5 pages.

Fingertip Pulse Oximeter SPO2 Monitor Oxygen Oximeter; Copyright 1995-2010, accessed at: http://74.125.45.132/search?q=cache:ANfHne9je7gJ:cgi.ebay.com.sg/ws/eBayISAPI.dII%3FViewItem%26item%3D260412542031+"Fingertip+Pulse+Oximeter+SPO2+Monitor+Oxigen+Oximeter"&cd=2&hl=en&ct=clnk&gl=us; 6 pages.

Handheld Pulse Oximeter PM-60A, Contec Medical System Co. Ltd., Jul. 31, 2009; accessed at: http://www.tradeindia.com/selloffer/1858593/Handheld-Pulse-Oximeter-PM-60A.html; 5 pages.

International Search Report and Written Opinion in PCT/US2010/048450 dated Apr. 12, 2011, 9 pages.

International Search Report and Written Opinion in PCT/US2013/031582 mailed Jun. 28, 2013, 11 pages.

mCare 300 Vital Signs Monitor, Spacelabs Medical, Inc., Copyright 2006, 4 pages.

Multiple Vital Signs from One Non-invasive Sensor, Starr™ Life Sciences Corp., Copyright 2009, accessed at: http://www.starrlifesciences.com/mouseox.html; 1 page.

Nag et al., Wireless E-jacket ofr Multiparameter Biophysical Monitoring and Telemedicine Applications, Medial Devices and Biosensors, 2006, 3rd IEEE/EMBS Inernational Summer School, Sep. 4-6, 2006, pp. 40-44.

NTIA Handheld Pulse Oximeter, Frontline Systems; Dec. 31, 2009, accessed at: http://www.tradeindia.com/fp385774/NTIA-Handheld-Pulse-Oximeter.html; 3 pages.

O'Donoughue et al., Design and Implementation of a Framework for Monitoring Patients in Hospitals Using Wireless Sensors in Ad Hoc configuration, Engineering in Medicine and Biology Society, EMBS '06, 28th Annual International Confernece of the IEEE, vol., No., Aug. 30, 2006-Sep. 3, 2066, pp. 6449-6452.

U.S. Appl. No. 61/243,872, filed Sep. 18, 2009 expired, of record.

Ultraview DM3—Dual Mode Vital Signs Monitor, Spacelabs Healthcare, Copyright 2010, 4 pages.

International Search Report and Written Opinion in PCT/US2013/031342 mailed Jun. 24, 2013, 12 pages.

Portable Patient Monitors, Welch Allyn, Copyright 2005-2006 MedDirect, Copyright 2005-2006, accessed at: http://www.meddirect.co.nz/Product.aspx?ProductId=3476; 1 page.

U.S. Appl. No. 29/417,592, filed Apr. 5, 2012 (specification and drawings).

U.S. Appl. No. 29/417,611, filed Apr. 5, 2012 (specification and drawings).

Station—Dictionary.com, [online], retrieved on Sep. 2, 2014, Retrived from, <URL: http://dictionary.reference.com/browse/station>, 4 pages.

* cited by examiner

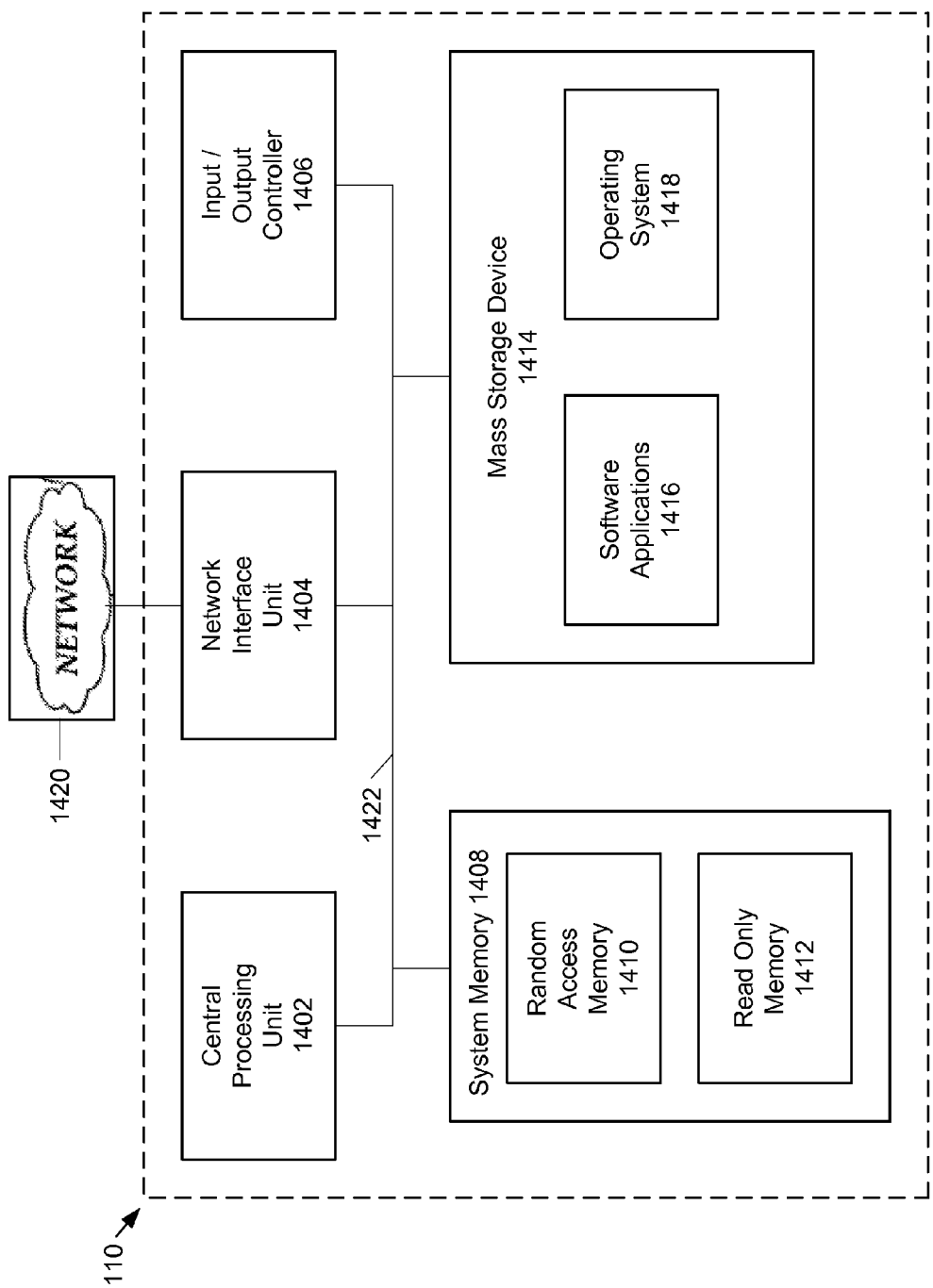

COMBINED EPISODIC AND CONTINUOUS PARAMETER MONITORING

BACKGROUND

In a medical setting, different monitoring devices may be used to monitor different types of patients. Surgical patients and post-surgical patients in intensive care are typically connected to monitoring devices that continuously receive physiological data from these patients. Less acute patients may be monitored less frequently using vital signs devices, for example when a clinician periodically takes vital signs for the patients.

Physiological and other data obtained from these patients are often stored and displayed in different places. For example, systems that continuously monitor patients typically display patient data and also send the data to an electronics medical records (EMR) system where the data is stored. For less acute patients, monitoring devices, for example vital signs devices, may be portable and data from these devices may be obtained manually, written on a chart and put outside a patient's room.

SUMMARY

Embodiments of the disclosure are directed to systems and methods for displaying physiological data on a medical display device. On the medical display device, one or more first units of physiological data are received from a first monitoring device. At least one of the first units of physiological data is received on a continuous basis. Each first unit of physiological data corresponds to a medical parameter being monitored by the first monitoring device. One or more second units of physiological data are received from a second monitoring device. At least one of the second units of physiological data is received on a non-continuous basis. Each second unit of physiological data corresponds to a medical parameter being monitored by the second monitoring device. The first and second units of physiological data are displayed on a single display screen of the medical display device.

The details of one or more techniques are set forth in the accompanying drawings and the description below. Other features, objects, and advantages of these techniques will be apparent from the description, drawings, and claims.

DESCRIPTION OF THE DRAWINGS

FIG. 14 shows example physical components of the central monitoring station of FIG. 1.

DETAILED DESCRIPTION

The present disclosure is directed to a central monitoring station that displays both continuous and episodic data for a plurality of patients. Continuous data refers to patient data that is continuously obtained at short intervals, for example on a millisecond or second basis. Episodic data refers to patient data that is obtained as needed, for example at intervals that may range from minutes to hours. The central monitoring station is typically located at a central nurse's station so that the plurality of patients may be monitored from a central location.

Continuous data is typically obtained for acute patients, for example from surgical patients or from post-surgical patients in an intensive care unit. Typically these patients are connected to a monitoring device that continually receives physiological data from these patients. Examples of continuous physiological data include blood pressure, temperature, pulse rate, oxygen saturation level (SPO2), end tidal carbon dioxide (ETCO2) and respiratory rate. Other types of physiological data are possible. The physiological data is typically displayed on the monitoring device, typically located near the patient, and sent to an EMR system where the data is stored.

Episodic data is typically obtained for less acute patients, for example a patient recovering from surgery but out of intensive care. For these patients, physiological data may be obtained via a vital signs device that may be manually operated by a clinician. In this disclosure, episodic data refers to data obtained on a non-continuous basis. Examples of episodic data obtained from the vital signs device include blood pressure, temperature, pulse rate and SPO2. Other examples of episodic data are possible. Episodic data such as blood pressure, temperature, pulse rate and SPO2 may also be obtained on a continuous basis. However, when this data is obtained at random intervals, for example when a nurse manually takes a patient's blood pressure and temperature, the data is designated as episodic data. A nurse may manually obtain an oxygen saturation reading by manually clipping an SPO2 sensor to the patient and monitoring the SPO2 via a vital signs device.

Figure 1:
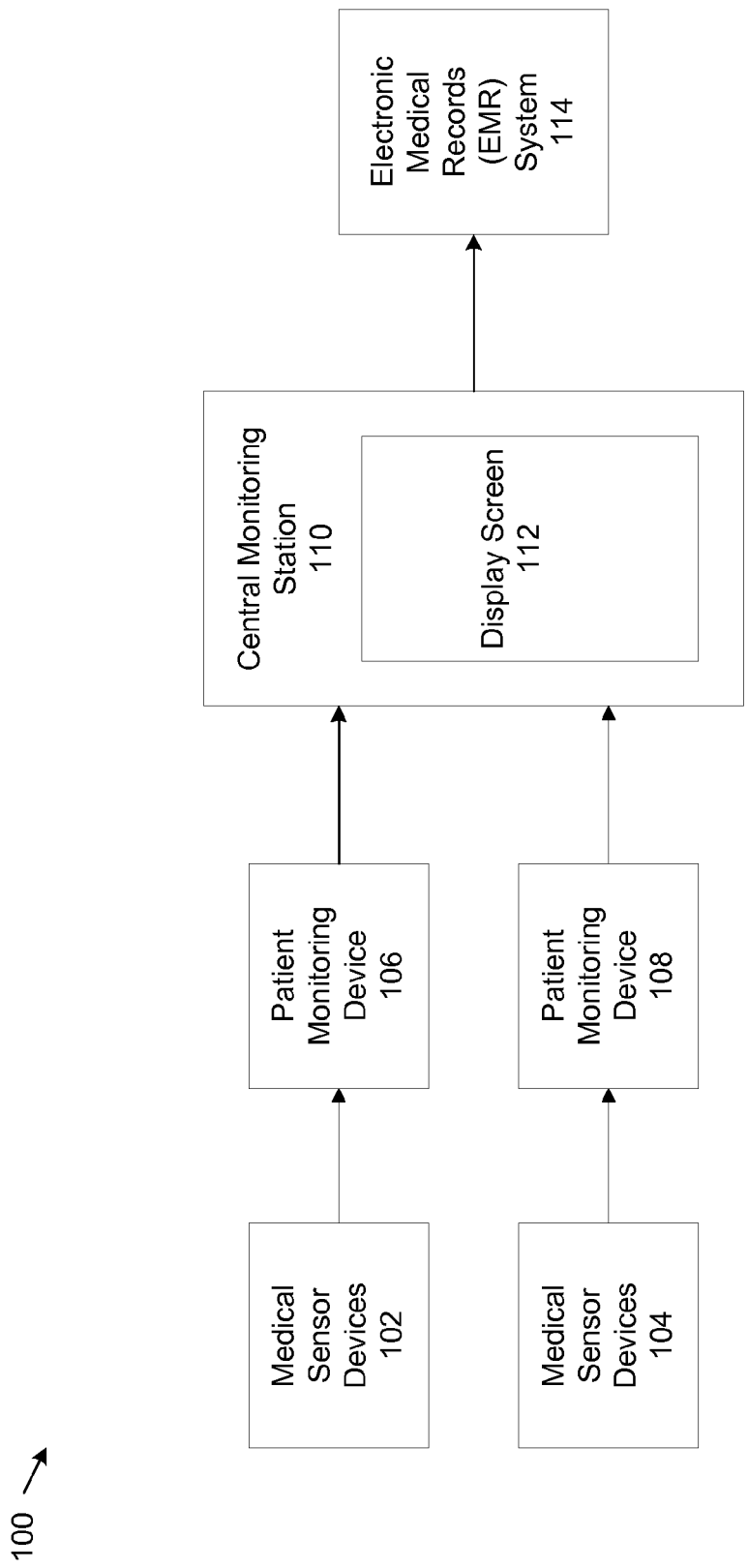
FIG. 1 shows an example patient monitoring system that supports a central monitoring station for displaying both continuous and episodic physiological data from a patient.

FIG. 1 shows an example system 100 that supports a central monitoring station for displaying both continuous and episodic physiological data from a patient. The example system 100 includes medical sensor devices 102 and 104, patient monitoring devices 106 and 108, central monitoring station 110 and EMR system 114. More or fewer medical sensor devices and patient monitoring devices may be used.

In the example system 100, medical sensor devices 102 are attached to a patient requiring continuous monitoring, for example a surgical patient or a post-surgical patient in an intensive care unit. The example patient monitor device 106 is a continuous monitoring device, receiving continuous physiological data from medical sensor devices 102. In this example, continuous physiological data refers to physiological data obtained at short intervals. Certain physiological data, for example SPO2 and pulse rate, may be obtained in millisecond intervals. Other physiological data, for example non-invasive blood pressure (NIBP) may be obtained at longer intervals, for example every few minutes. An example continuous monitoring device is the Welch Allyn 1500 Patient Monitor from Welch Allyn, Inc. of Skaneateles Falls, N.Y.

In the example system 100, medical sensor devices 104 are attached to a patient receiving non-continuous episodic monitoring. For example, a patient monitor device 108 may include some or all of the medical sensor devices 104, for example a thermometer, a blood pressure cuff and an SPO2 sensor. The patient monitor device 108 may be a portable vital signs device administered by a clinician on an as needs basis. An example vital signs device is the Connex® Vital Signs Monitor from Welch Allyn, Inc. of Skaneateles Falls, N.Y.

The example central monitoring station 110 receives physiological data from patient monitor device 106 and from patient monitor device 108 and displays the physiological data on example display screen 112. In addition, the central monitoring station 110 sends physiological data received from patient monitoring devices 106 and 108 to EMR system 114.

Figure 2:
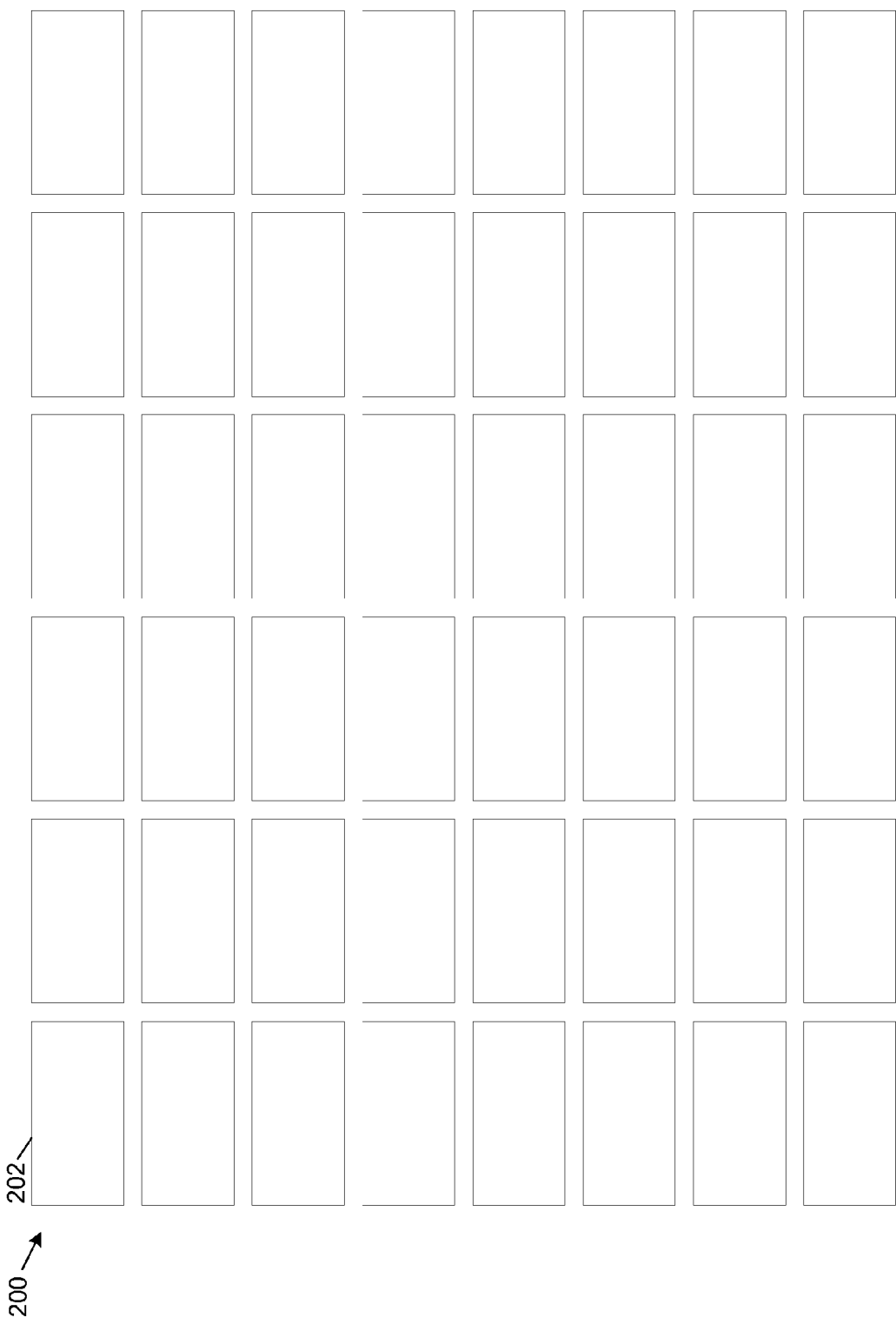
FIG. 2 shows an example user interface of the central monitoring station of FIG. 1.

FIG. 2 shows an example user interface 200 of display screen 112. The example user interface 200 includes a rendering of 48 display tiles. Each display tile provides information about an individual patient. Each display tile identifies the person, provides a location for the patient, for example a hospital room number, and displays physiological data for the patient. Different types of tiles are possible, including a continuous tile, an episodic tile, a trend tile, an empty room tile and a waiting area tile. The example user interface 200 shows six rows of tiles with eight tiles per row. Other tile organizations are possible and more or fewer than 48 tiles may be displayed. For example, an alternative tile organization is to render 36 display tiles, organized into six rows of six tiles per row. Each tile has a standard layout, as explained later herein.

In examples, the position of each tile on the user interface 200 may be configured via one or several modes. In an example automatic mode, the tiles are positioned by room number. In this mode, a tile with the lowest numerical room number is positioned at the upper left portion of the user interface 200 and a tile with the highest numerical room number is position in the lower right portion of the user interface 200. In an example batch mode, certain positions on the user interface 200 are reserved for certain room numbers. Then, when a patient is assigned a room number, the tile takes a reserved position on the user interface 200. In an example manual mode, tiles can be manually positioned anywhere on the user interface 200.

Figure 3:
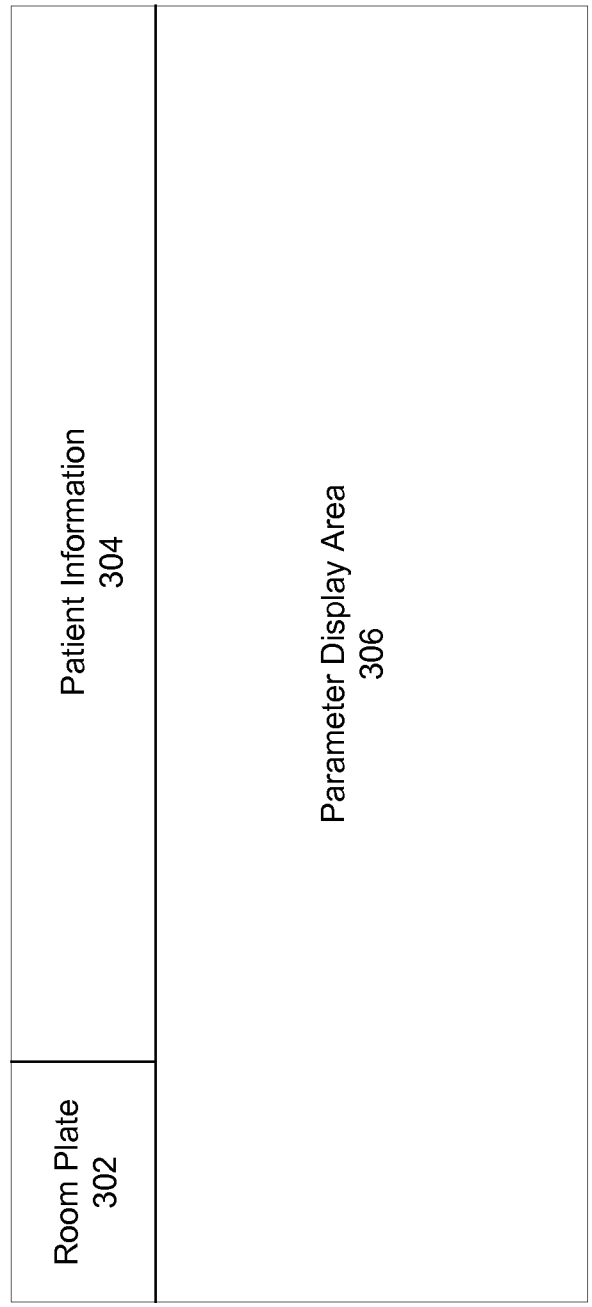
FIG. 3 shows an example standard layout for a display tile of the user interface of FIG. 2.

FIG. 3 shows an example standard layout of display tile 202. The standard layout for display tile 202 includes a room plate area 302, a patient information area 304 and a parameter display area 306. The room plate area 302 typically displays a room number for a patient. In examples the room plate area 302 may also include a hospital unit number and a bed number. The patient information area 304 includes identification information for the patient including the patient's name and sex. Other information may be included in the patient information area 304. The parameter display area 306 displays physiological parameter data for the different types of tiles, as explained herein.

Figure 4:
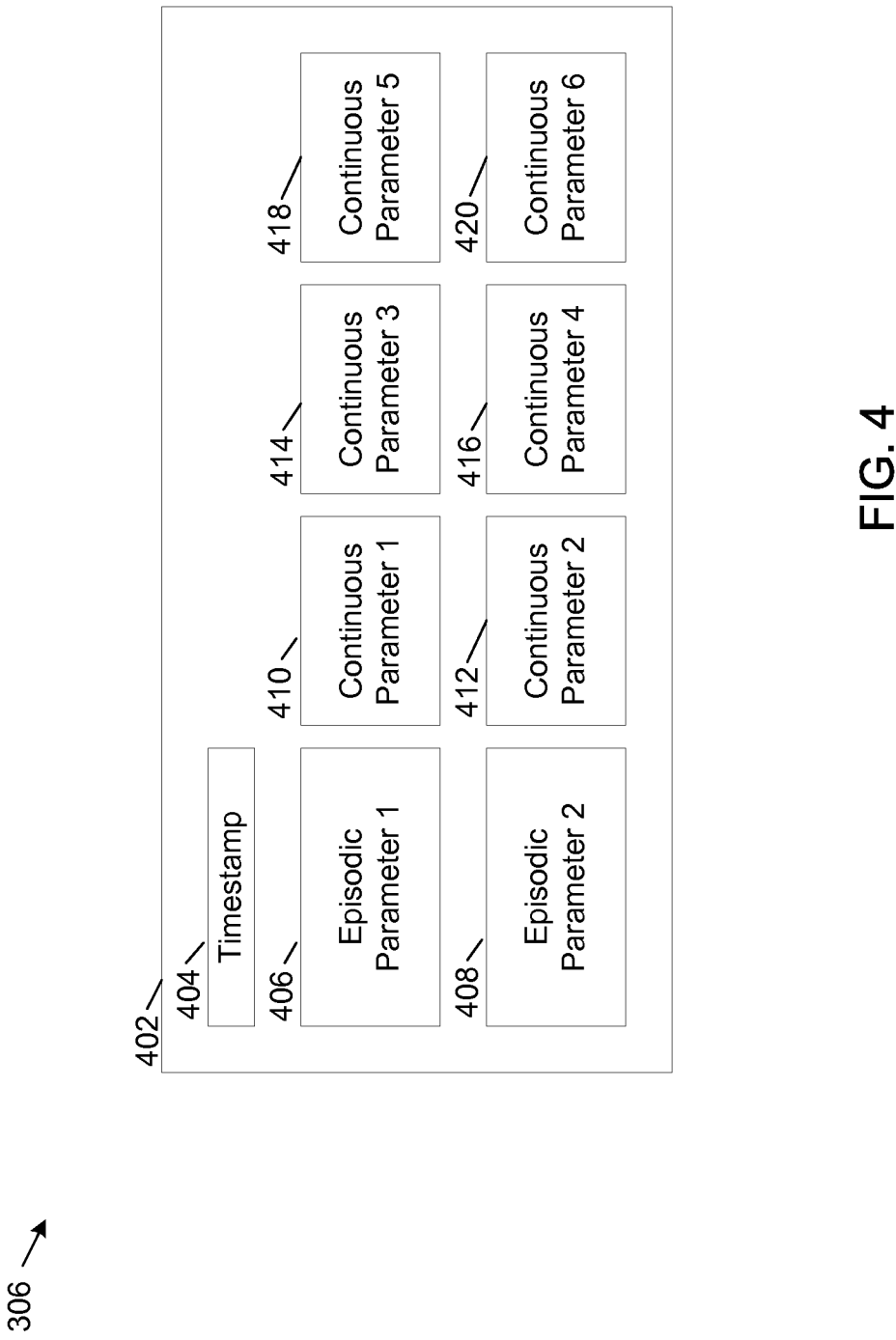
FIG. 4 shows an example display screen for a continuous tile.

FIG. 4 shows an example display screen 402 for a continuous tile that is displayed in parameter display area 306. A continuous tile is a tile that is associated with a medical device that continuously monitors physiological data for a patient. However, a continuous tile may display both continuous and episodic parameter data. The display screen 402 shows a layout having two episodic parameters and six continuous parameters. The continuous tile shown in display screen 402 includes a timestamp 404, episodic parameters 406 and 408 and six continuous parameters 410, 412, 414, 416, 418 and 420. Each parameter represents a specific type of physiological data for the patient. More or fewer episodic and continuous parameters may be displayed in parameter display area 306 for a continuous tile.

Figure 5:
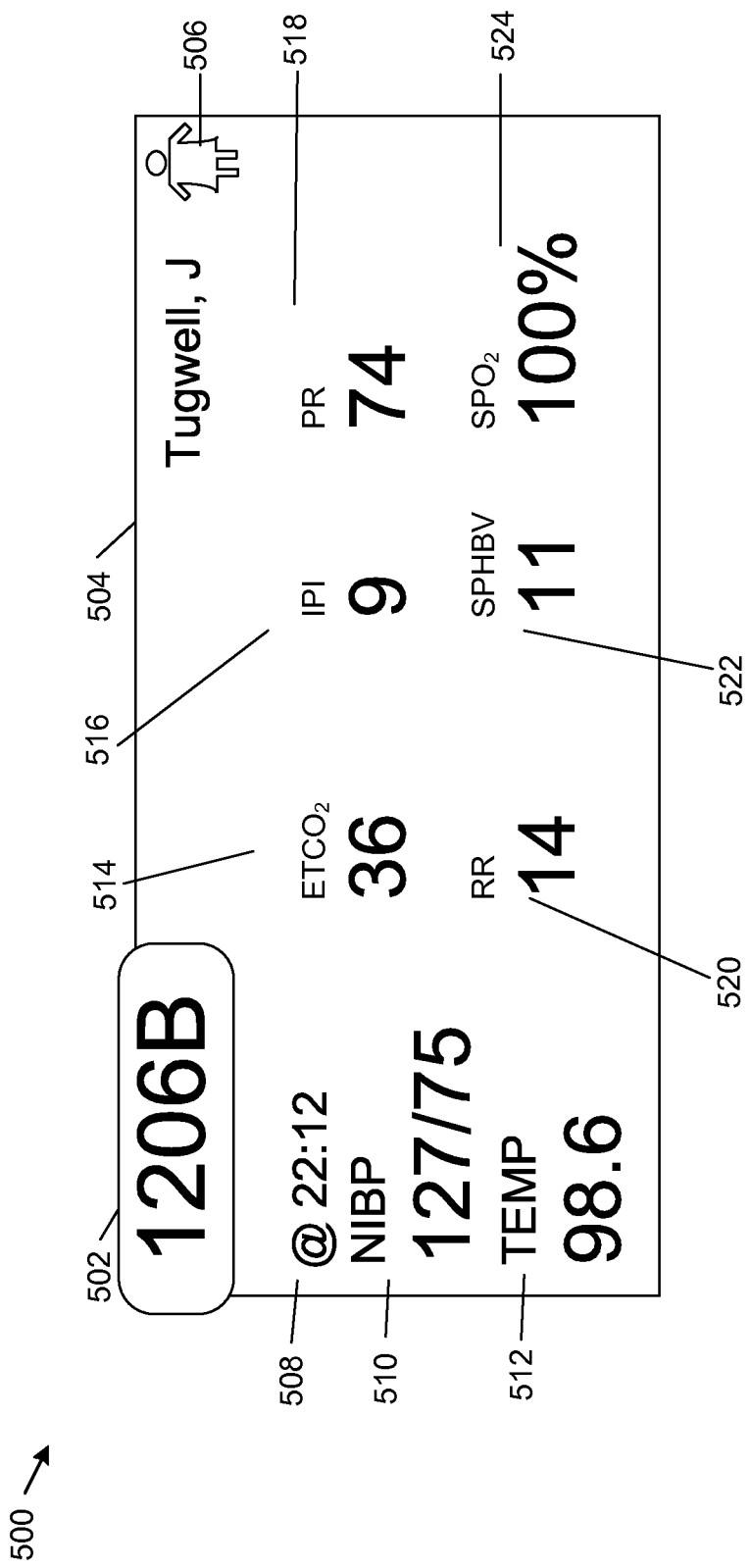
FIG. 5 shows an example screenshot of a continuous tile.

FIG. 5 shows an example screen shot for a continuous tile 500 with two episodic parameters and six continuous parameters. The continuous tile 500 includes room plate designator 502, patient information including the name 504 of the patient, in this example Tugwell, J. and the sex of the patient, in this case an icon 506 indicating that the patient is a woman. The continuous tile 500 includes timestamp 508. The two episodic parameters include parameters for non-invasive blood pressure (NIBP) 510 and temperature 512. The six continuous parameters include parameters for end tidal carbon dioxide (ETCO2) 514, IPI (integrated pulmonary index) 516, pulse rate (PR) 518, respiratory rate (RR) 520, venous calibrated total hemoglobin (SPHBV) 522 and oxygen saturation (SPO2) 524.

Figure 6:
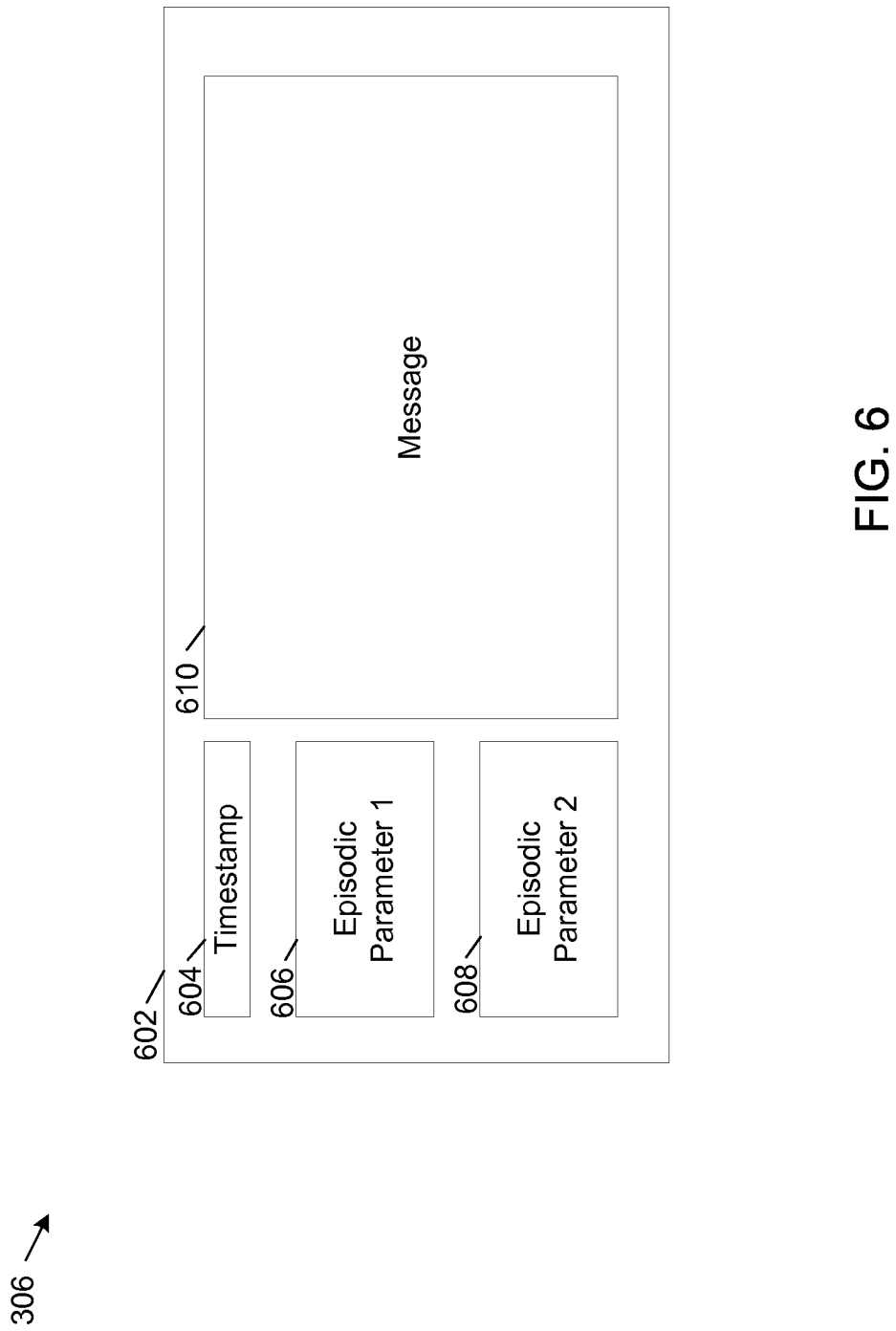
FIG. 6 shows an example display screen for a continuous tile with continuous data temporarily stopped.

FIG. 6 shows an example display screen 602 for a continuous tile that is displayed in parameter display area 306. For the example display screen 602, continuous data has been temporarily stopped. The display screen 602 shows that when continuous data is stopped, instead of displaying continuous tiles, a message 610 is displayed in the area of parameter display area 306 reserved for the display of continuous tiles. The message indicates that that continuous data has been stopped temporarily. For example, a patient may be temporarily disconnected from a monitoring device to go the bathroom, get an x-ray, etc. The message may also indicate a reason why the continuous data has been stopped and may indicate an expected time when continuous data may resume. The display screen 602 still shows a timestamp 604 and two episodic parameters 606 and 608.

Figure 7:
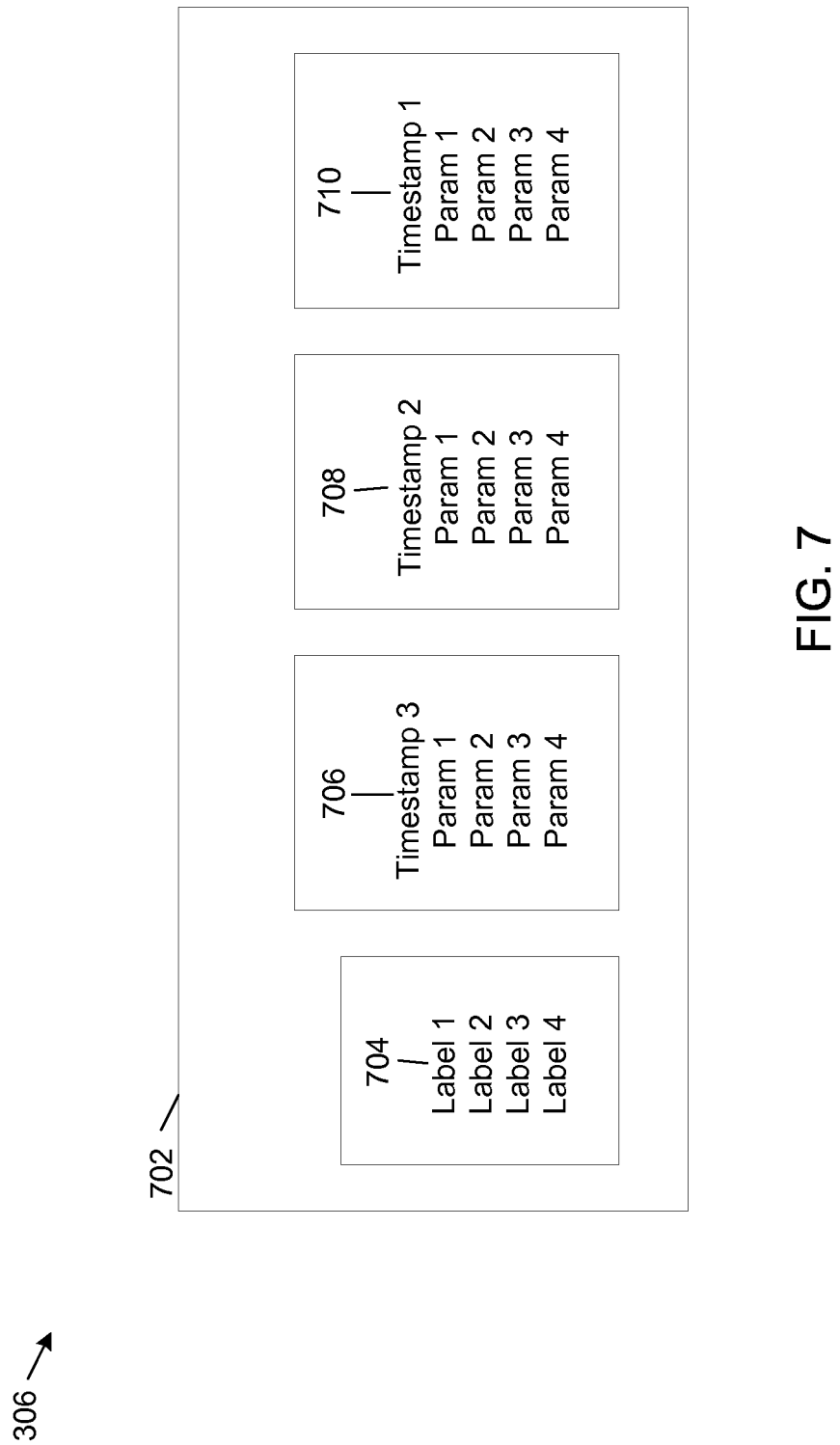
FIGS. 7-8 show example display screens for trend tiles.

FIG. 7 shows an example display screen for a trend tile 702 with three columns of data that is displayed in parameter display area 306. A trend tile is displayed when a patient steps down from being continuously monitored, but still needs monitoring at relatively short intervals, for example every 15 minutes. The trend tile shows on one screen trends in the parameters being monitored. For example, trend tile 702 includes a column 704 that provides labels for four parameters being monitored. In addition, trend tile 702 includes three columns 706, 708 and 710 of data. Column 706 includes timestamp 3, representing the latest data obtained. Column 710 includes timestamp 1, representing the earliest data being displayed. Column 708 shows parameter data corresponding to a timestamp between the latest and earliest. By viewing trend tile 702, a clinician may be able to see a trend in the values of parameters being monitored.

Figure 8:
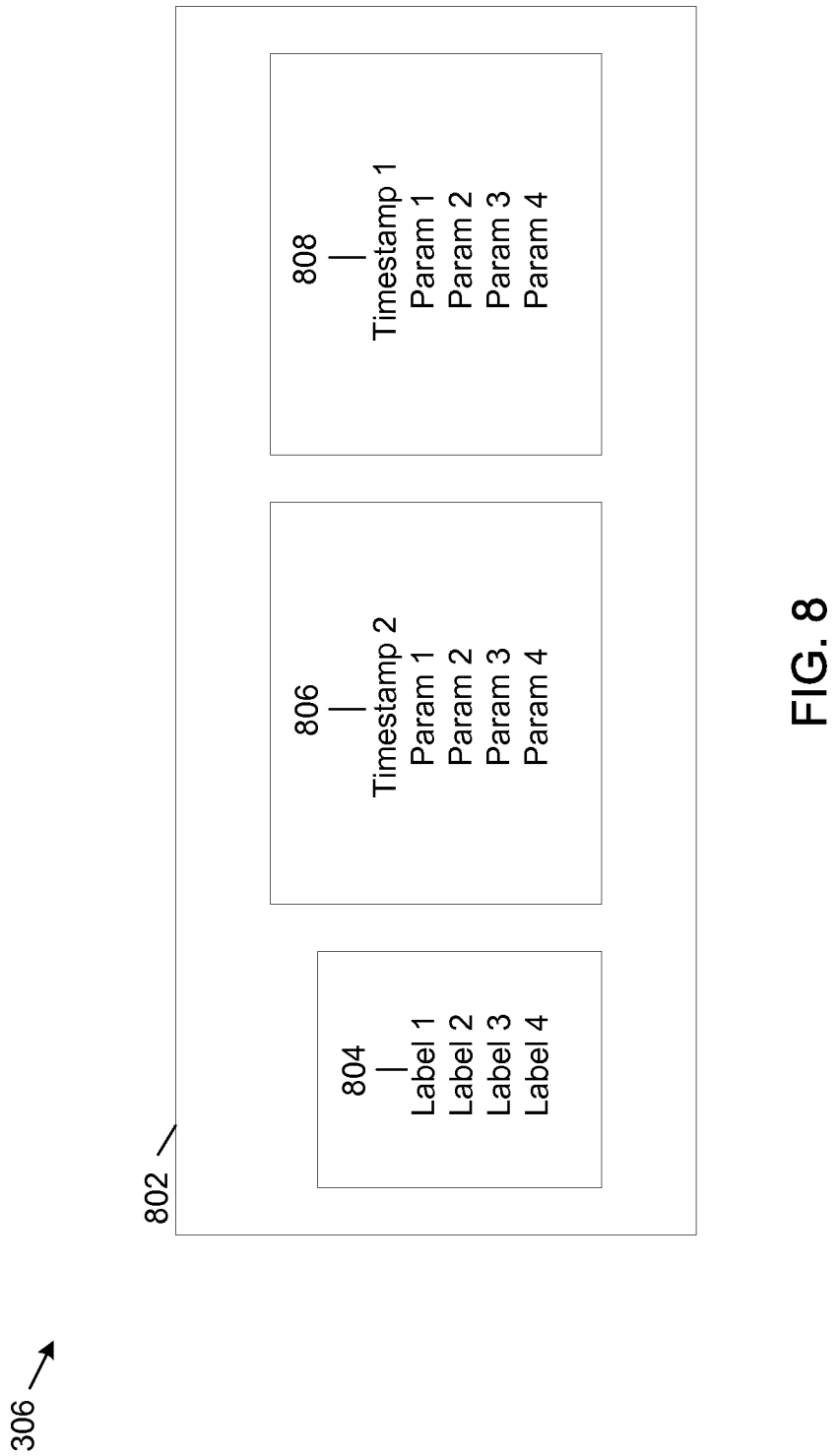

FIG. 8 shows an example display screen for a trend tile 802 with two columns of data that is displayed in parameter display area 306. Trend tiles with more than three columns of data are possible.

Figure 9:
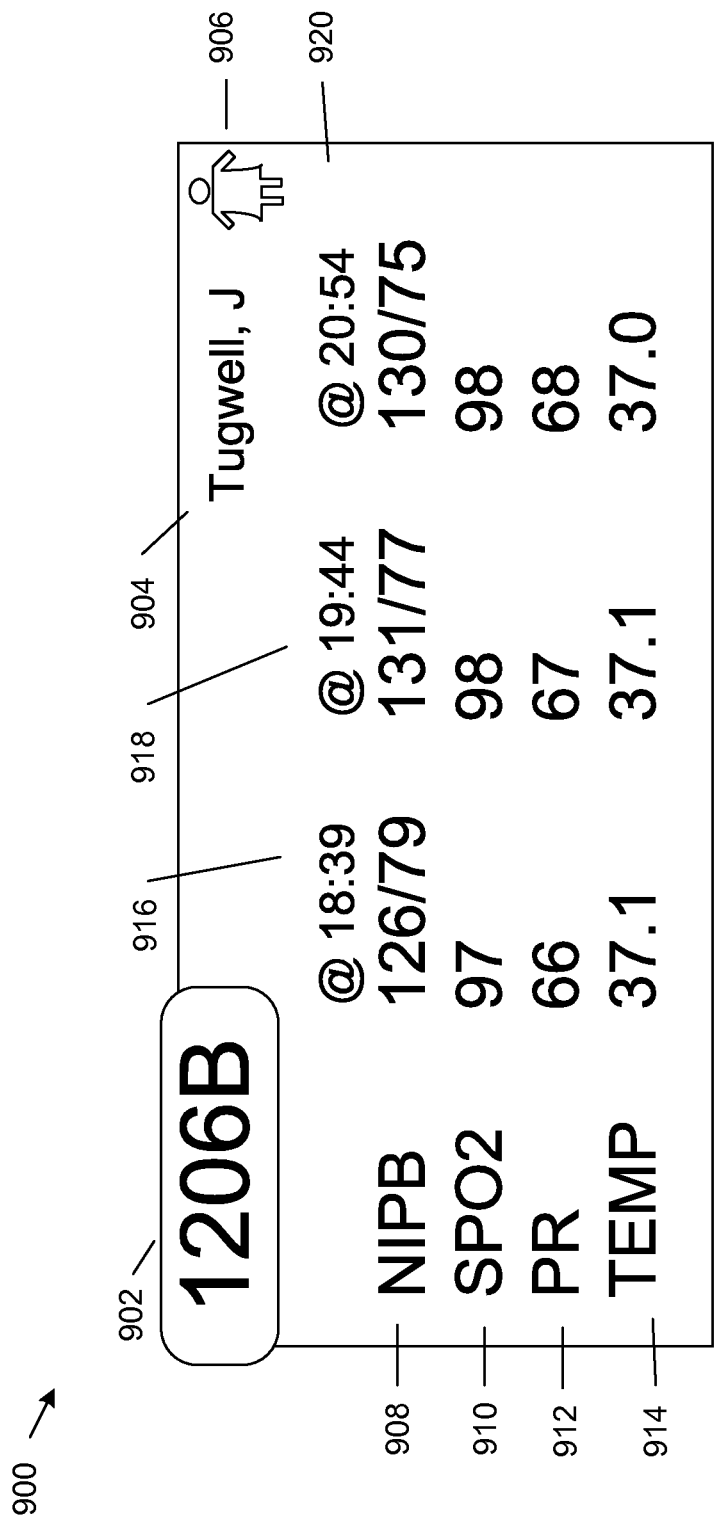
FIG. 9 shows an example screenshot of a trend tile.

FIG. 9 shows an example screen shot for a trend tile 900 for four episodic parameters with three columns of parameter data. The trend tile 900 includes room plate designator 902, patient information including the name 904 of the patient, in this example Tugwell, J. and the sex of the patient, in this case an icon 906 indicating that the patient is a woman. The trend tile 900 displays data for four episodic parameters including non-invasive blood pressure (NIBP) 908, oxygen saturation (SPO2) 910, pulse rate (PR) 912 and temperature (TEMP) 914. The trend tile 910 includes values of these four episodic parameters for three different timestamps 916, 918 and 920. For the example trend tile 900, the timestamp 916 corresponds to the earliest parameter data displayed and timestamp 920 corresponds to the latest parameter data displayed. For example, timestamp 916 corresponds to readings taken for the four parameters 908-914 at a time of 18:39, timestamp 918 corresponds to readings taken for the four parameters 908-914 at a time of 19:44 and timestamp 920 corresponds to readings taken for the four parameters 908-914 at a time of 20:54.

Figure 10:
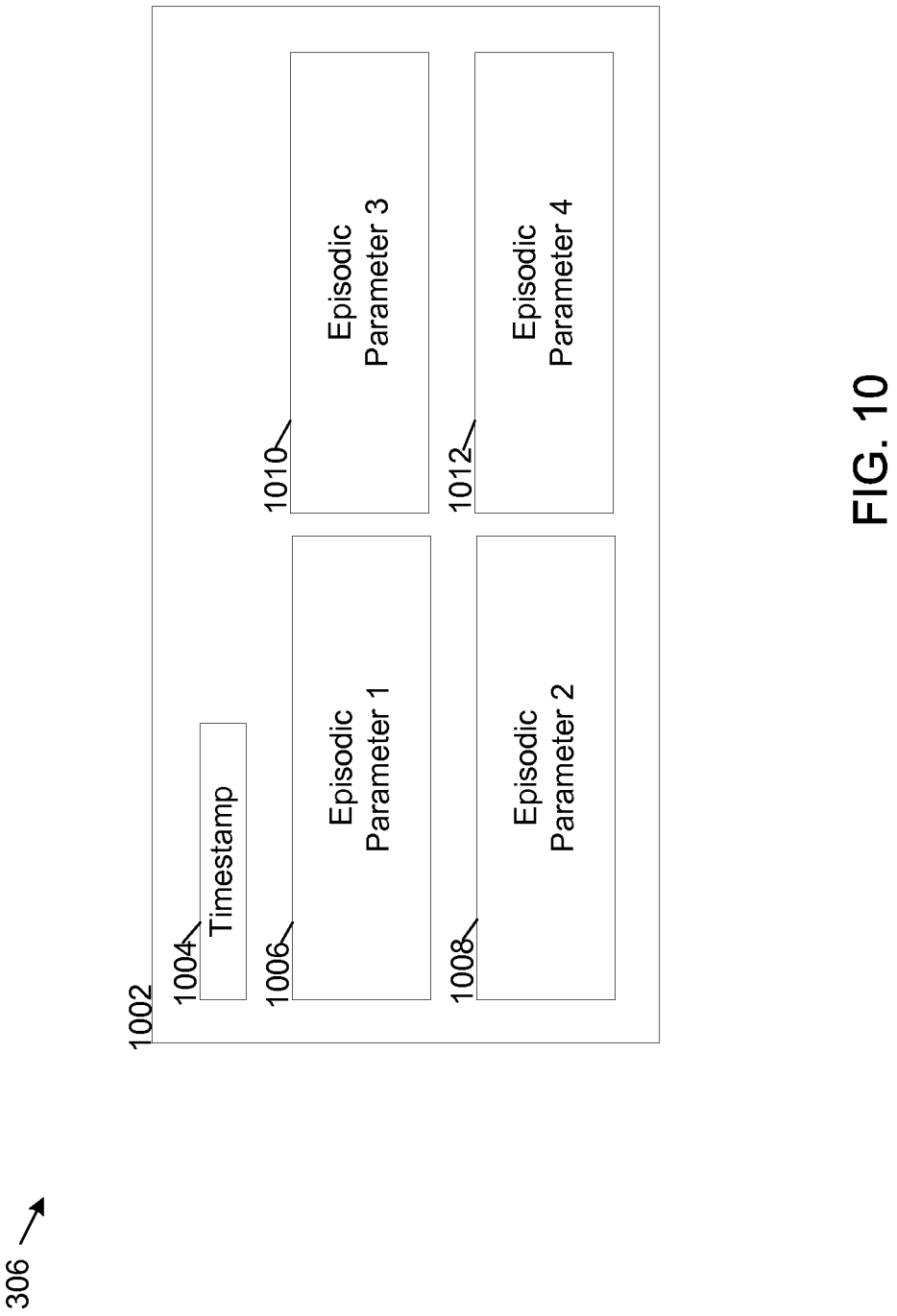
FIG. 10 shows an example display screen for an episodic tile.

FIG. 10 shows an example display screen for an episodic tile 1002 that is displayed in parameter display area 306. The episodic tile 1002 includes four episodic parameters 1006, 1008, 1010 and 1012. The episodic tile 1002 is displayed when the central monitoring station 110 does not receive parameter data for a predetermined period of time, for example for 90 minutes. In a typical hospital scenario, continuous tiles are displayed for surgical and post-surgical patients. When patients step-down from being continuously monitored to being monitored at longer intervals, for example every 15 minutes, trend tiles are typically displayed. When the condition of a patient is less acute, the patient is typically monitored at still longer intervals, for example once per nursing shift. When physiological data for a patient is not received by the central monitoring station within the still longer time interval, for example 90 minutes, an episodic tile is typically displayed for that particular patient.

Figure 11:
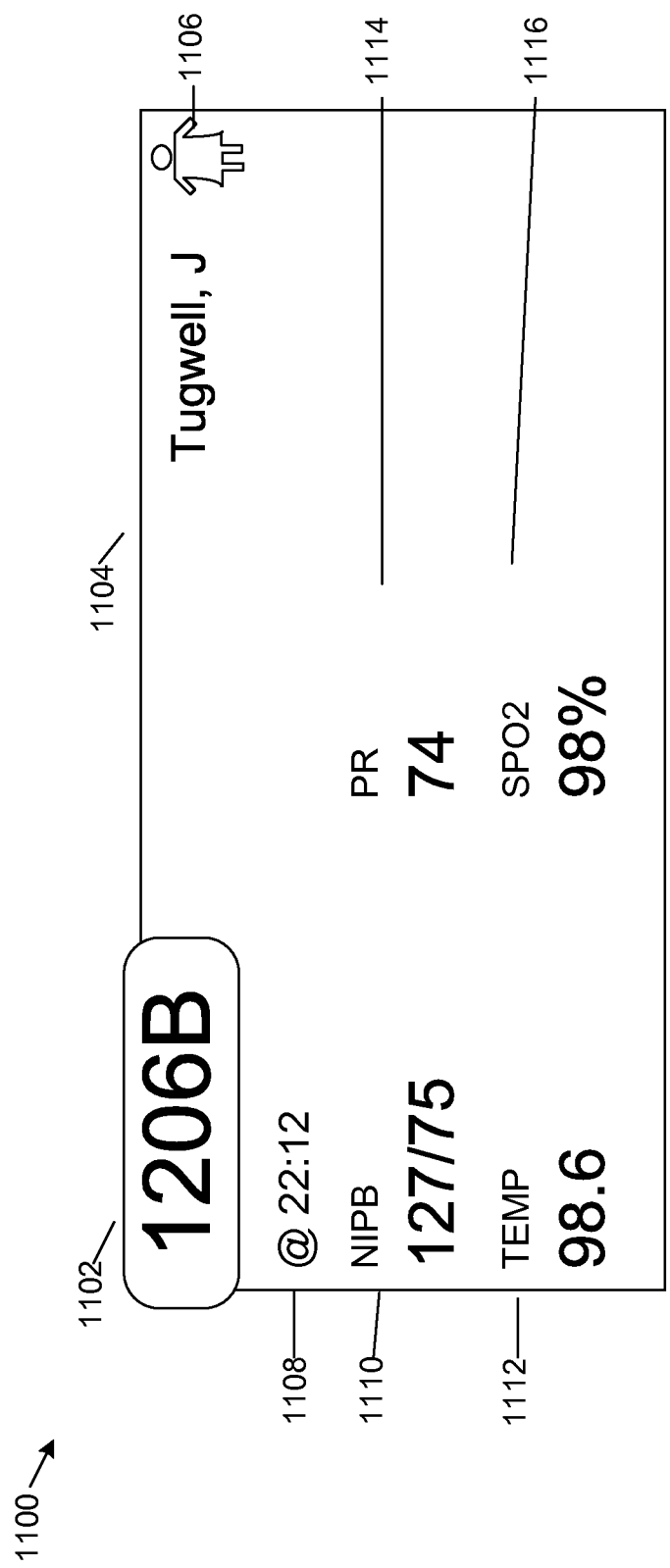
FIG. 11 shows an example screenshot for a trend an episodic tile.

FIG. 11 shows an example screen shot for an episodic tile 1100 with four episodic parameters. The episodic tile 1100 includes room plate designator 1102, patient information including the name 1104 of the patient, in this example Tugwell, J., and the sex of the patient, in this case an icon 1106 indicating that the patient is a woman. The episodic tile 1100 includes timestamp 1108. The four episodic parameters include parameters for non-invasive blood pressure (NIBP) 1110, temperature 1112, pulse rate 1114 and SPO2 1116.

Figure 12:
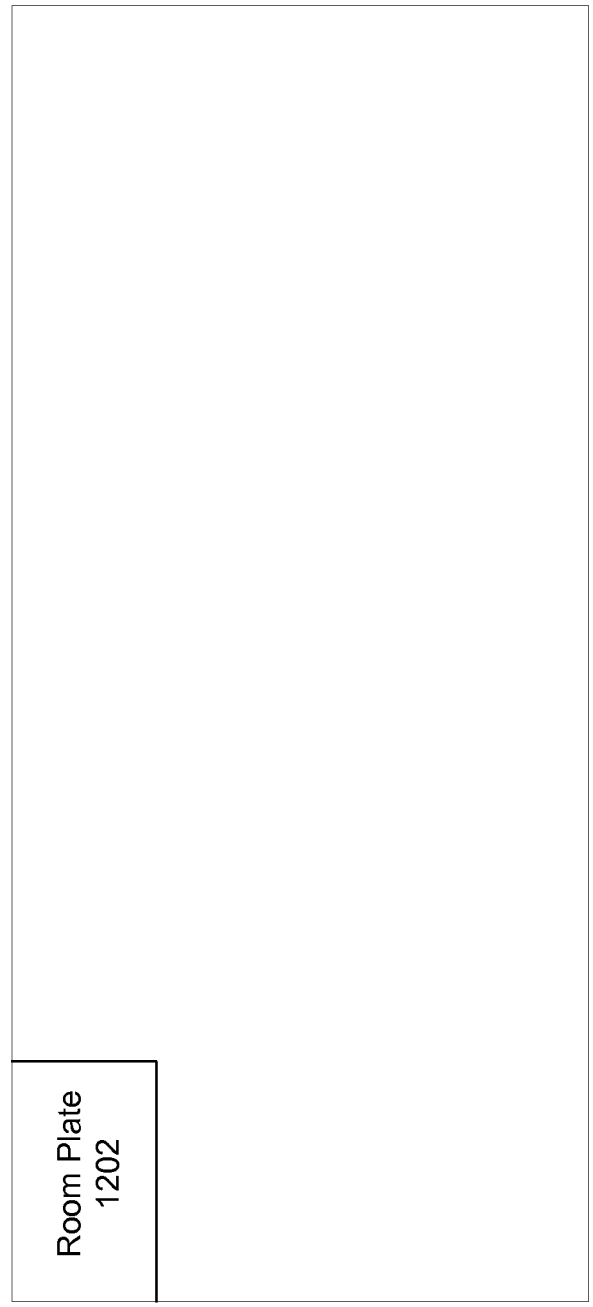
FIG. 12 shows an example display screen for an empty room tile.

FIG. 12 shows an example display screen for empty room tile 1200. The example empty room tile 1200 is a tile for a patient that has been admitted to a hospital and has been assigned a room number, but physiological data has not been taken and entered into the central monitoring station for the patient yet. When one or more medical devices are associated with the patient and physiological data is taken for the patient, the empty room tile 1200 becomes a standard tile—for example a continuous time, a trend tile or an episodic tile.

Figure 13:
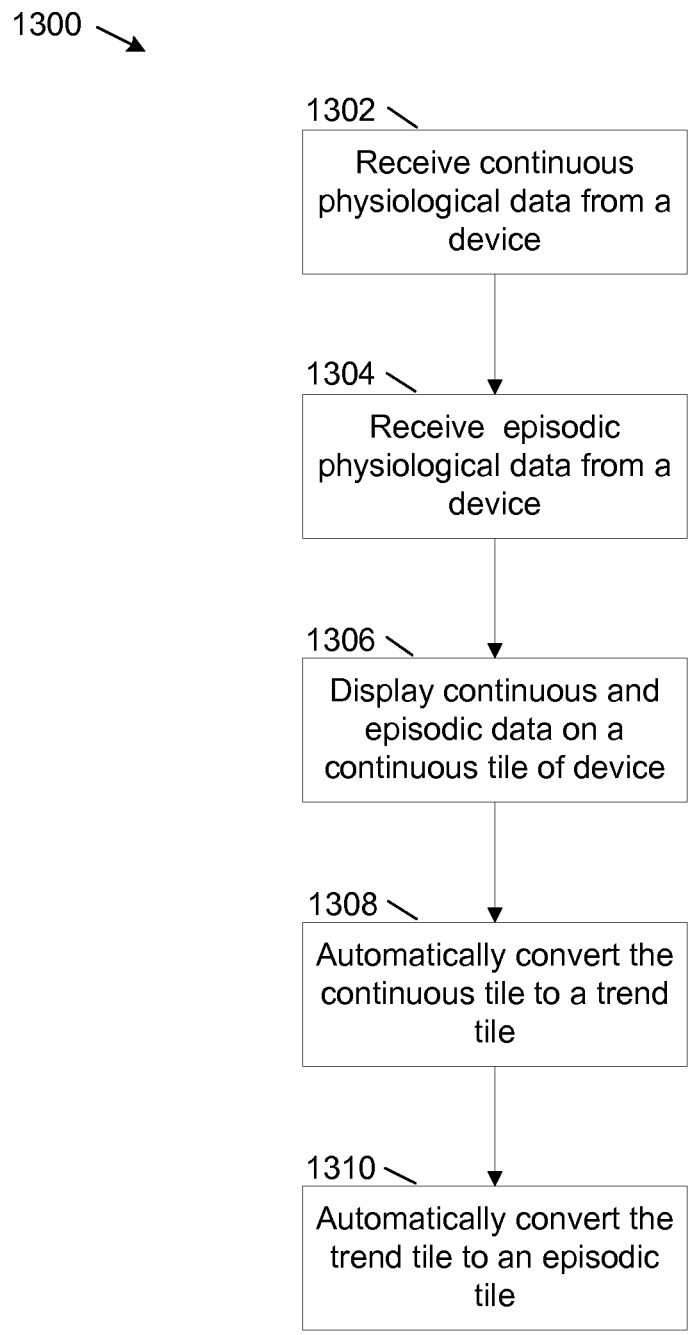
FIG. 13 shows an example flowchart of a method for displaying continuous and episodic physiological data for a patient on a single display device.

FIG. 13 shows an example flowchart for a method 1300 for displaying continuous and episodic physiological data for a patient on a single display device. At operation 1302, continuous physiological data is received from a first monitoring device. The first monitoring device is a patient monitoring device that is connected to one or more physiological sensors attached to a patient. The patient monitoring device is typically used for acute patients, typically patients in surgery or in an intensive care unit. The physiological sensors continuously monitor physiological data for the patient. Examples of physiological data that is continuously monitored for such acute patients include temperature, blood pressure, pulse rate, oxygen saturation, respiratory rate and end tidal carbon dioxide. Other continuous physiological data is possible. The patient monitoring device is located near the patient and includes a display screen on which the physiological data can be observed by clinicians.

At operation 1304, episodic physiological data for the patient is obtained from a second patient monitoring device. As discussed, episodic physiological data refers to patient data that is obtained as needed, for example taken manually by a clinician at random time intervals. The second patient monitoring device is typically a vital signs device, for example the Connex® Vital Signs Monitor from Welch Allyn, Inc. of Skaneateles Falls, N.Y. Examples of episodic data include blood pressure, temperature, pulse rate and oxygen saturation. Other episodic physiological data is possible.

At operation 1306, the continuous physiological data and the episodic physiological data are displayed on a continuous tile of a centrally located medical display device. The central located medical display device, for example central monitoring station 110, is typically located at a nurse's station, whereby clinicians can view the status of a plurality of patients. The central monitoring station 110 can display a plurality of display tiles, each tile corresponding to one patient. The continuous tile, an example screenshot of which is shown in FIG. 5, displays both continuous parameters and episodic parameters for a patient on a single tile.

A continuous tile is displayed for a patient when continuous physiological data continues to be received for the patient. At operation 1308, when the central monitoring station 110 does not receive continuous physiological data within a first predetermined time interval, for example 15 minutes, the continuous tile is automatically converted to a trend tile. The trend tile, an example screenshot of which is shown in FIG. 9, displays multiple columns of episodic data, each column of episodic data representing a snap shot of the episodic data at a specific time. By viewing the trend tile, a clinician may be able to detect changes in episodic data over time.

When a patient no longer needs acute monitoring, for example, when the patient is out of intensive care and moved to a standard hospital room, the patient is typically monitored at less frequent intervals. For example, the patient's vital signs may be taken during changes of nursing shifts or at random intervals during a nurse's shift. At operation 1310, when the central monitoring station 110 does not receive any new physiological data from the patient within a second predetermined time interval, for example 90 minutes, the trend tile is automatically converted to an episodic tile. The episodic tile, an example screenshot of which is shown in FIG. 11, displays the most recently received episodic data.

FIG. 14 illustrates example physical components of the central monitoring station 110. As illustrated in the example of FIG. 14, the central monitoring station 110 includes at least one central processing unit ("CPU") 1402, a system memory 1408, and a system bus 1422 that couples the system memory 1408 to the CPU 1402. The system memory 1408 includes a random access memory ("RAM") 1410 and a read-only memory ("ROM") 1412. A basic input/output system contains the basic routines that help to transfer information between elements within the central monitoring station 110, such as during startup, is stored in the ROM 1412. The central monitoring station 110 further includes a mass storage device 1414. The mass storage device 1414 is able to store software instructions and data.

The mass storage device 1414 is connected to the CPU 1402 through a mass storage controller (not shown) connected to the bus 1422. The mass storage device 1414 and its associated computer-readable data storage media provide non-volatile, non-transitory storage for the central monitoring station 110. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the central monitoring station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the central monitoring station 110.

According to various embodiments of the invention, the central monitoring station 110 may operate in a networked environment using logical connections to remote network devices through the network 1420, such as a local network, the Internet, or another type of network. The central monitoring station may connect to the network 1420 through a network interface unit 1404 connected to the bus 1422. It should be appreciated that the network interface unit 1404 may also be utilized to connect to other types of networks and remote computing systems. The central monitoring station 110 also includes an input/output controller 1406 for receiving and processing input from a number of other devices, including a keyboard, a mouse, a touch user interface display screen, or another type of input device. Similarly, the input/output controller 1406 may provide output to a touch user interface display screen, a printer, or other type of output device.

As mentioned briefly above, the mass storage device 1414 and the RAM 1410 of the central monitoring station 110 can store software instructions and data. The software instructions include an operating system 1418 suitable for controlling the operation of the central monitoring station 110. The mass storage device 1414 and/or the RAM 1410 also store software instructions, that when executed by the CPU 1402, cause the central monitoring station 110 to provide the functionality of the central monitoring station 110 discussed in this document. For example, the mass storage device 1414 and/or the RAM 1410 can store software instructions that, when executed by the CPU 1402, cause the central monitoring station 110 to display the user interface 200 screen and other screens.

The description of the example physical components used on the central monitoring station 110 as shown in FIG. 14 also applies to example physical components used in the EMR system 114. Thus, each of the one or more computing devices in the EMR system 114 includes at least one central processing unit ("CPU"), a system memory, and a system bus that couples the system memory to the CPU. The system memory also includes a random access memory ("RAM"), a read-only memory ("ROM") and a mass storage device that is able to store software instructions and data. In addition, the mass storage device and its associated computer-readable data storage media provide non-volatile, non-transitory storage for each of the one or more computing devices in the EMR system 114.

The various embodiments described above are provided by way of illustration only and should not be construed to limiting. Various modifications and changes that may be made to the embodiments described above without departing from the true spirit and scope of the disclosure.

What is claimed is:

1. A method for displaying physiological data on a medical display device, the method comprising:
    on the medical display device, receiving one or more first units of physiological data from a first monitoring device, at least one of the first units of physiological data being received on a continuous basis, each first unit of physiological data corresponding to a medical parameter being monitored by the first monitoring device;
    receiving one or more second units of physiological data from a second monitoring device, at least one of the second units of physiological data being received on a non-continuous basis, each second unit of physiological data corresponding to a medical parameter being monitored by the second monitoring device;
    displaying the first and second units of physiological data on a single display screen of the medical display device;
    measuring a first time interval;
    when the first time interval expires without receiving the first units of physiological data, automatically converting a continuous tile showing first continuous data to a trend tile, the trend tile displaying one or more columns of the first units of physiological data;
    measuring a second time interval, the second time interval being greater than the first time interval; and
    when the second time interval expires without receiving the first units of physiological data, automatically converting the trend tile to an episodic tile, the episodic tile displaying the first units of physiological data received non-continuously.

2. The method of claim 1, wherein the medical display device displays the first and second units of data in a series of display tiles on the medical display device.

3. The method of claim 2, wherein the display tiles are organized by rows and columns.

4. The method of claim 2, wherein the display tiles include continuous tiles, episodic tiles and trend tiles.

5. The method of claim 4, wherein the continuous tiles include a display of physiological data received continuously and physiological data received non-continuously.

6. The method of claim 4, wherein the episodic tiles include a display of physiological data received non-continuously and do not include a display of physiological data monitored continuously.

7. The method of claim 4, wherein the trend tiles include displays of two or more groups of second units of physiological data, the two or more groups of physiological data corresponding to physiological data received non-continuously, each group of second unit of physiological data being identified by a timestamp.

8. The method of claim 1, wherein the first time interval is 15 minutes.

9. The method of claim 1, wherein the second time interval is 90 minutes.

10. The method of claim 4, wherein a message is displayed on the continuous tiles when a patient is temporarily disconnected from the first monitoring device.

11. The method of claim 1, wherein the medical parameters corresponding to the first units of physiological data include blood pressure, temperature, pulse rate, end tidal carbon dioxide, respiratory rate, hemoglobin, oxygen saturation and an index related to pulmonary health for a patient.

12. The method of claim 1, wherein the medical parameters corresponding to the second units of physiological data include blood pressure, temperature, pulse rate and oxygen saturation.

13. An electronic computing device comprising:
    a processing unit; and
    system memory, the system memory including instructions that when executed by the processing unit cause the electronic computing device to:
        receive one or more first units of physiological data from a first monitoring device, at least one of the first units of physiological data being received on a continuous basis, each first unit of physiological data corresponding to a medical parameter being monitored by the first monitoring device;

receive one or more second units of physiological data from a second monitoring device, at least one of the second units of physiological data being received on a non-continuous basis, each second unit of physiological data corresponding to a medical parameter being monitored by the second monitoring device;

display the first and second units of physiological data on a single display screen of the electronic computing device;

measure a first time interval;

when the first time interface expires without receiving the first units of physiological data, automatically convert a continuous tile showing first continuous data to a trend tile when the first units of physiological data are not received within a first time interval, the trend tile displaying one or more columns of the first continuous data, with each column representing a snapshot of episodic data at a specific time;

measure a second time interval, the second time interval being greater than the first time interval; and when the second time interval expires without receiving the first units of physiological data, automatically convert the trend tile to an episodic tile, the episodic tile displaying both:
- the first units of physiological data received non-continuously; and
- the second units of physiological data received non-continuously.

14. The electronic computing device of claim 13, wherein the processing unit causes the electronic computing device to display the first and second units of physiological data in a series of display tiles on the electronic computing device, the display tiles including continuous tiles, episodic tiles and trend tiles.

15. The electronic computing device of claim 14, wherein the processing unit causes the electronic computing device to display one or more first units of physiological data and one or more second units of physiological data in a continuous tile.

* * * * *